US011897860B2

(12) United States Patent
Carrasco et al.

(10) Patent No.: US 11,897,860 B2
(45) Date of Patent: Feb. 13, 2024

(54) DIRECT SYNTHESIS OF CYCLIC CARBONATES USING CHOLINE CHLORIDE AS CATALYST UNDER MILD CONDITIONS

(71) Applicant: Baker Hughes Oilfield Operations LLC, Houston, TX (US)

(72) Inventors: Analette Carrasco, Missouri City, TX (US); Jerry J. Weers, Richmond, TX (US); Catherine C Blackwell, Fulshear, TX (US); Sankaran Murugesan, Katy, TX (US); Xiaofeng Wang, Katy, TX (US); Douglas Nugent, La Porte, TX (US); Corby A. Roberts, League City, TX (US)

(73) Assignee: Baker Hughes Oilfield Operations LLC, Houston, TX (US)

( * ) Notice: Subject to any disclaimer, the term of this patent is extended or adjusted under 35 U.S.C. 154(b) by 0 days.

(21) Appl. No.: 17/694,287

(22) Filed: Mar. 14, 2022

(65) Prior Publication Data

US 2023/0286936 A1 Sep. 14, 2023

(51) Int. Cl.
*C07D 317/16* (2006.01)
*C07D 317/38* (2006.01)
*B01J 31/02* (2006.01)

(52) U.S. Cl.
CPC ........ *C07D 317/38* (2013.01); *B01J 31/0239* (2013.01); *C07C 2527/24* (2013.01)

(58) Field of Classification Search
CPC .......................... B01J 31/0239; C07D 317/16
See application file for complete search history.

(56) References Cited

FOREIGN PATENT DOCUMENTS

| | | | | | |
|---|---|---|---|---|---|
| CN | 101130537 A | * | 2/2008 | | |
| CN | 101130537 A | | 2/2008 | | |
| JP | 05-202022 A | | 8/1993 | | |
| JP | 05202022 A | * | 8/1993 | ........... | C07D 317/36 |
| KR | 10-2002-0066819 A | | 6/2003 | | |
| WO | 2008128956 A1 | | 10/2008 | | |

OTHER PUBLICATIONS

Zhu, Anlian, et al. "Supported choline chloride/urea as a heterogeneous catalyst for chemical fixation of carbon dioxide to cyclic carbonates." Green Chem. (2007), 9, pp. 169-172. (Year: 2007).*
International Search Report and Written Opinion issued in connection with corresponding PCT Application No. PCT/US2023/015016 dated Jul. 7, 2023.
Amaral, A. J.R., et al., "Synthesis of bifunctional cyclic carbonates from CO2 catalysed by choline based systems", Tetrahedron Letters, 2013, vol. 54, pp. 5518-5522 abstract; pp. 5518-5520.
Calo, V. , et al., "Cyclic Carbonate Formation from Carbon Dioxide and Oxirane in Tetrabutylammonium Halides as Solvent and Catalyst", Organic Letters, Jun. 29, 2002, vol. 4, No. 15, 2561-2563.
He, Q., et al., "Synthesis of Cyclic Carbonates from CO2 and Epoxides using Ionic Liquids and Related Catalysts Including Choline Chlo-ride-Metal Halide Mixtures", Catalysis Science & Technology, May 15, 2014, vol. 4, Issue 6, 1513, 16pp.
Li, Q, et al., "Synthesis of Cyclic Carbonates from Urea and Diols over Metal Oxides", Catalyst Today, Jun. 20, 2006, vol. 115, 111-116.
Pescarmona, P., "Cyclic Carbonates Synthesized from CO2: Applications, Challenges and Recent Trends", Current Opinion in Green and Sustainable Chemistry, Feb. 2021, vol. 29, No. 16, 100457, 1-9.
Rehman, A., et al., "Recent Advances in the Synthesis of Cyclic Carbonates via CO2 Cycloaddi-tion to Epoxides", Journal of Environmental Chemical Engineering, Jan. 2021 Vol. 9, No. 2, 105113, 1-28.
Sakakura, T., et al., "Transformation of Carbon Dioxide", Chern. Reviews, Jun. 13, 2007, vol. 107, No. 6, 2365-2387.
Vagnoni, M., et al., "Choline-Based Eutectic Mixtures as Catalysts for Effective Synthesis of Cyclic Carbonates from Epoxides and CO2". Journal of CO2 Utilization, Dec. 2020, vol. 42, 101302, 1-7.
Zhou, J. , et al., "Synthesis of Propylene Carbonate from Urea and 1,2-Propylene Glycol over Metal Carbonates", Chemical Industry and Chemical Engineering Quarterly, Jul. 2011, vol. 17, 323-331.

* cited by examiner

*Primary Examiner* — John S Kenyon
(74) *Attorney, Agent, or Firm* — Crowe & Dunlevy, P.C.

(57) ABSTRACT

A method for direct synthesis of cyclic carbonates is achieved by reacting at least one epoxide with carbon dioxide in the presence of a choline catalyst, such as choline chloride, under mild conditions such as a temperature between about 25° C. to 150° C. and a pressure of from about atmospheric to 75 psi (0.52 MPa), in a cyclic carbonate solvent. The choline catalyst may be the only catalyst used, and a co-catalyst or hydrogen bond donor is not necessary. The concentration of choline catalyst in the solvent ranges from about 0.5 mol % to about 10 mol %, based on the epoxide.

19 Claims, 1 Drawing Sheet

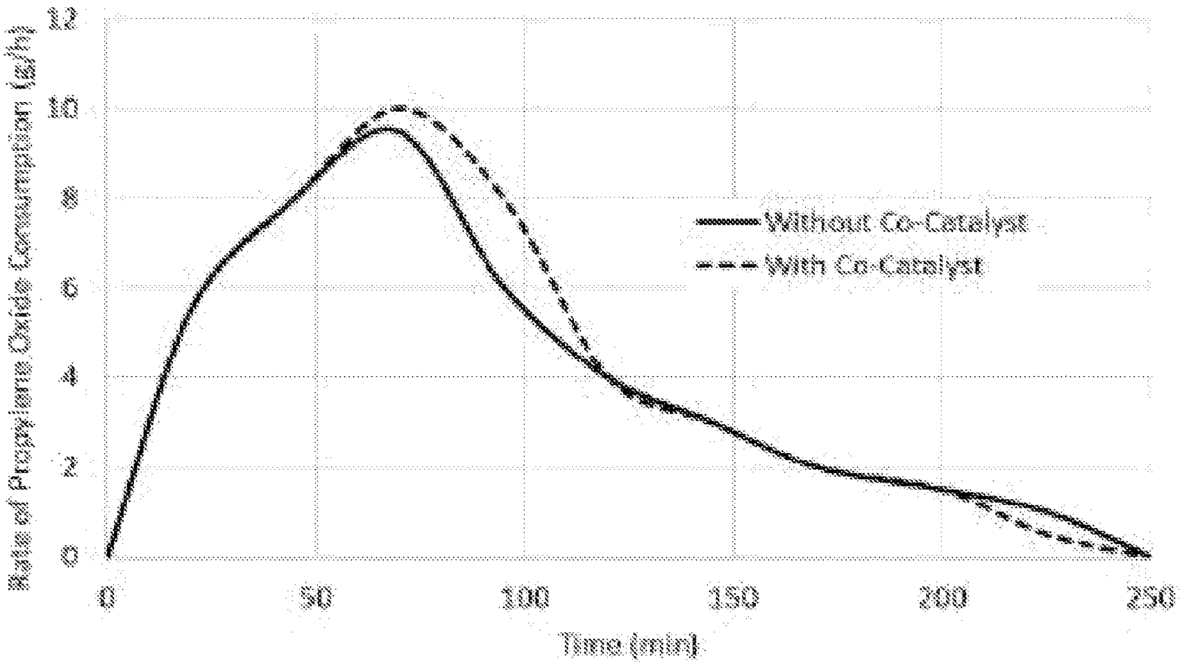
Rate of Propylene Oxide Consumption (g/h)
12
10
8
6
4
2
0
0
50
100
150
200
250
Time (min)
Without Co-Catalyst
With Co-Catalyst

DIRECT SYNTHESIS OF CYCLIC CARBONATES USING CHOLINE CHLORIDE AS CATALYST UNDER MILD CONDITIONS

TECHNICAL FIELD

The present invention relates to methods for manufacturing cyclic carbonates, and more particularly relates to methods for methods for directly synthesizing cyclic carbonates under mild conditions.

BACKGROUND

Cyclic carbonates are of great interest due to their utilization as environ-ment-friendly/biodegradable solvents in diverse applications including, but not necessarily limited to, batteries for electronics, cosmetics, cleaning agents, etc. In general, organic carbonates are known to be prepared using direct and indirect methods using a wide range of catalysts and reaction conditions.

Indirect methods such as transesterification of urea have the disadvantage of utilizing inorganic catalysts and excess alcohol reagents leading to lower product purity and intricate purification procedures. See for instance Q. L I et al., "Synthesis of Cyclic Carbonates from Urea and Diols over Metal Oxides", *Catalyst Today,* 20 Jun. 2006, Vol. 115, 111-116, and J. ZHOU et al., "Synthesis of Propylene Carbonate from Urea and 1,2-Propylene Glycol over Metal Carbonates", *Chemical Industry and Chemical Engineering Quarterly*, July 2011, Vol. 17, 323-331.

While direct methods utilize the reaction between epoxides and carbon dioxide and significant work has been reported in literature, an efficient manufacturing process that combines the use of a low-cost, nontoxic, single catalyst system at low concentrations under mild process conditions has yet to be reported. See for example V. CALO et al., "Cyclic Carbonate Formation from Carbon Dioxide and Oxirane in Tetrabutylammonium Halides as Solvent and Catalyst", *Organic Letters,* 29 *Jun.* 2002, Vol. 4, No. 15, 2561-2563; A. REHMAN et al., "Recent Advances in the Synthesis of Cyclic Carbonates via $CO_2$ Cycloaddition to Epoxides", *Journal of Environmental Chemical Engineering*, January 2021 Vol. 9, No. 2, 105113; and Q. H E et al., "Synthesis of Cyclic Carbonates from $CO_2$ and Epoxides using Ionic Liquids and Related Catalysts Including Choline Chloride-Metal Halide Mixtures", *Catalysis Science & Technology,* 15 May 2014, Vol. 4, Issue 6, 1513.

Literature references indicate choline by itself or without a hydrogen bond donor does not catalyze the reaction of epoxides with carbon dioxide to directly synthesize cyclic carbonates. See M. VAGNONI et al., "Choline-Based Eutectic Mixtures as Catalysts for Effective Synthesis of Cyclic Carbonates from Epoxides and $CO_2$," *Journal of $CO_2$ Utilization*, December 2020, Vol. 42, 101302.

Further, reaction of carbon dioxide with glycols in direct methods of synthesizing cyclic carbonates disadvantageously utilize extreme process conditions of high temperatures (>150° C.) and pressures (>200 psi (>1.4 MPa)). See T. SAKAKURA, et al., "Transformation of Carbon Dioxide," *Chem. Reviews,* 13 *Jun.* 2007, Vol. 107, No. 6, 2365-2387; and P. PESCARMONA, "Cyclic Carbonates Synthesized from $CO_2$: Applications, Challenges and Recent Trends", *Current Opinion in Green and Sustainable Chemistry*, February 2021, Vol. 29, No. 16, 100457. In addition, most of the catalysts used in the direct process are either toxic, expensive, in high concentrations and used with other catalysts (co-catalyst).

Thus, it would be desirable to develop a new method for the direct synthesis of cyclic carbonates that can be conducted under mild conditions yet which give good reaction rates. It would also be desirable if the method were relatively low cost, nontoxic, and was practical and sustainable.

SUMMARY

There is provided, in one form, a method for direct synthesis of cyclic carbonates which method includes reacting at least one epoxide with carbon dioxide in the presence of a choline catalyst at a temperature between about 25° C. to 150° C. and a pressure of from about atmospheric to 75 psi, in a cyclic carbonate solvent, where the choline catalyst is selected from the group consisting of choline chloride, choline bromide, choline iodide, choline bitartrate, choline citrate, and combinations thereof, and then recovering at least one cyclic carbonate product therefrom.

BRIEF DESCRIPTION OF THE DRAWINGS

The FIGURE is a graph of the rate of propylene oxide consumption over time comparing the reaction rate of propylene oxide with $CO_2$ with and without a co-catalyst at 1.4 mol % catalyst with respect to propylene oxide, 130° C., and 45 psi (0.31 MPa).

DETAILED DESCRIPTION

It has been discovered that cyclic carbonates may be synthesized directly from epoxides and carbon dioxide ($CO_2$) in a carbonate solvent system utilizing relatively low amounts of a choline catalyst. The novel and unique manufacturing process avoids the use of a co-catalyst or hydrogen bond donor, which can complicate purification of the end product as well as add expense to the process.

The manufacturing process is general and can be used to give a variety of cyclic carbonate products including, but not necessarily limited to, propylene carbonate (PC), ethylene carbonate (EC), styrene carbonate (SC), glycerol carbonate (GC), and others. During the research on the process, it was also discovered the choline catalyst was at least partially oxyalkylated under the reaction conditions used. This catalyst is new and potentially helps keep the reaction rates high due to its good solubility in the cyclic carbonates being produced.

Previous processes used expensive and toxic catalysts, and thus the methods are not practical and sustainable. Additionally, high catalyst loading and the requirement of co-catalysts in the conventional processes can result in low product purity and/or complex product purification. Furthermore, prior methods require high temperatures and pressures which can only be attained by sophisticated and expensive manufacturing design and construction.

In contrast, the method discovered as described herein uses a choline catalyst, such as choline chloride, which is a common feed additive and is readily biodegradable:

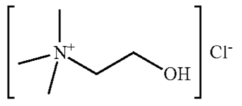

Additionally, the choline catalyst can be used in relatively low concentrations, and can be used without a co-catalyst or hydrogen bond donor. Furthermore, mild reaction conditions of low temperatures and pressures are employed. In non-limiting embodiments, "low temperature" is defined herein as a temperature below 150° C., alternatively as a temperature below 120° C., and "low pressure" is defined herein as a pressure below 50 psi (0.34 MPa).

More specifically, the catalyst in the present method can include, but is not necessarily limited to, choline chloride, choline bromide, choline iodide, choline bitartrate, choline citrate, and combinations thereof. It was discovered that not all choline salts are effective catalysts, thus these choline salts are not included in the group of suitable catalysts. For example, in the reaction of propylene oxide with CO2 in propylene carbonate solvent, choline bicarbonate only gave polypropylene glycol as a product. It is believed salts with strongly basic anions such as hydroxide, carbonate or bicarbonate are not good catalyst as they promote polymerization of the epoxide.

In some experiments, choline bitartrate gave some propylene carbonate in the reaction with propylene oxide, but the reaction was slow and gave a number of unidentified byproducts. However, choline catalysts such as choline bitartrate and choline citrate may still be effective under different test conditions or combinations.

Choline chloride is the least expensive catalyst of those recited above, and as will be shown, it gives near quantitative conversion of propylene oxide (PO) to propylene carbonate and gives the fastest reaction rates under the low pressure conditions shown in the Examples.

As noted, the synthesis method herein works without a co-catalyst or hydrogen bond donor. As previously discussed, the literature suggests that a hydrogen bond donor is required for PO and $CO_2$ to react to form cyclic carbonates. For instance, M. VAGNONI et al., "Choline-Based Eutectic Mixtures as Catalysts for Effective Synthesis of Cyclic Carbonates from Epoxides and $CO_2$," *Journal of $CO_2$ Utilization*, December 2020, Vol. 42, 101302 in Table 1 shows that choline chloride does not form styrene carbonate in the absence of a hydrogen donor such as glycerin, urea, or a carboxylic acid. Most reactions of an epoxide with $CO_2$ require high pressure and high temperatures as well as such a co-catalyst. The method described herein was surprisingly discovered to synthesize cyclic carbonates using a cyclic carbonate as a solvent which allows the reaction of $CO_2$ with an epoxide to proceed at a fast rate under mild conditions of low pressure and low temperature without a hydrogen bond donor (co-catalyst). Stated another way, the direct synthesis described herein is achieved with the choline catalyst as the only catalyst.

Suitable epoxide reactants include, but are not necessarily limited to, ethylene oxide, propylene oxide, styrene oxide, glycidol, epichlorohydrin, butylene oxides (e.g., 1,2-epoxybutane, 2,3-epoxy butane), cyclohexene oxide, 2,2 bis [p-(2,3 epoxypropoxy)phenyl] propane and polymers thereof (reaction products of bisphenol A and epichlorohydrin), alpha olefin epoxides i.e., 1,2-epoxydodecane and combinations thereof.

The molar ratio of epoxide to carbon dioxide ranges from about 1:1 to about 1:1.2. Technically the molar ratio of epoxide to carbon dioxide is about 1:1 for the stoichiometric reaction. Some $CO_2$ may be used to flush oxygen and/or moisture from the headspace of the reactor, but the actual amount used in the reaction itself is about 1:1 molar with the epoxide.

In one non-limiting embodiment, the temperature range for the method herein may range from about 25° C. independently to 150° C.; alternatively, from about 30° C. independently to about 145° C.; in another non-restrictive version from about 35° C. independently to about 140° C.; in a different range from about 40° C. independently to about 135° C.; in another non-limiting range from about 45° C. to about 130° C.; alternatively from about 50° C. independently to about 125° C.; and also from about 45° C. independently to about 120° C. As used herein with respect to a range, "independently" means that any given endpoint may be used together with any other given endpoint to provide a suitable range. For example, a suitable temperature range may be from about 45° C. to about 145° C.

With respect to reaction pressure, the reaction pressure may range from about atmospheric pressure (14.7 psi or 0.1 MPa) independently to about 75 psi (0.52 MPa); alternatively, from about 30 psi (0.21 MPa) independently to about 50 psi (0.34 MPa). In one non-limiting embodiment, epoxide and carbon dioxide are fed to the reactor simultaneously keeping total pressure within the limits above. The optimum rate of addition of the epoxide to a reactor ranges from about 0.08 lbs/min independently to 1.5 lbs/min, in another non-restrictive version, from about 0.10 independently to about 0.12 lbs/min while the carbon dioxide charge rate is controlled to between about 0.03 independently to 0.08 lbs/minute in one non-limiting embodiment, and alternatively from about 0.05 independently to about 0.06 lbs/minute. A batch using the following conditions: total PO charge is 10.52 h @0.1025 lb/min ave. while total $CO_2$ charge was 15.3 h @ 0.0563 lb/min ave. yielded propylene carbonate with greater than 98% purity for in a total batch time of **17*h***. This molar ratio was 1:1.05 PO/$CO_2$. The total pressure in the reactor as well as how fast the reagents are added are important to getting the optimum rate of carbonate formation.

As mentioned, it has been discovered that the direct synthesis is advantageously carried out in a cyclic carbonate solvent. Using a cyclic carbonate as a solvent helps dissolve the choline catalyst to initiate the reaction. This solvent type is also helpful when the epoxide reactant is in the form of a gas. The cyclic carbonate solvent may be different from, or the same as, the cyclic carbonate product being made. In one non-limiting embodiment, it can be helpful for the cyclic carbonate solvent to be the same as the cyclic carbonate product being synthesized because it can simplify later purification.

As noted, only relatively low concentrations of the choline catalyst are necessary. In a non-limiting example, the choline catalyst concentration in the cyclic carbonate solvent may range from about 0.3 mol % independently to about 10 mol %; alternatively, from about 0.5 mol % independently to about 9 mol %, in another non-restrictive version from about 1 mol % independently to about 5 mol %.

The concentration of the catalyst, e.g., choline chloride, varies as the reaction progresses. In a non-limiting embodiment, at the start of the reaction the concentration may be about 9 mol % (based on the amount of PO), which is diluted to about 3 mol % by the end of the reaction. In one non-limiting version, an effective amount of choline catalyst is that which maintains a concentration of from at least 1 mol % at the end of the reaction to at least 5 mol % to maintain an acceptable reaction rate.

In one non-limiting explanation, the choline catalyst is at least partially oxyalkylated under the reaction conditions. In particular, choline chloride has limited solubility in propylene carbonate at ambient temperature. While not wanting to be held to any particular theory, the oxyalkylation of the catalyst may improve the solubility of the catalyst in the carbonate solution. It is believed that the choline chloride catalyst as well as the oxyalkylated choline are effective catalysts in any recycling of the material.

In a different non-restrictive understanding, a small amount of the catalyst can be oxyalkylated or reacted in this process. However, this does not impact the overall process product yield or rate of reaction. At the end of the reaction, there can be some solid, unreacted catalyst that comes out of the reaction due to low solubility in the product that can be eventually reused. Some of the choline catalyst may be degraded in the process, and thus may need to be replaced. In other words, in some cases some small loss of catalyst is possible. If the catalyst is to be recycled, the amount of catalyst lost will need to be replaced for the next batch. The amount of degraded catalyst depends on reaction conditions and is greatest when the higher pressures, temperatures, catalyst loadings, and reaction times are present.

Advantages of the method described herein over conventional methods of synthesizing cyclic carbonates include, but are not limited to, the combined use of a low-cost, nontoxic, single catalyst under mild conditions to provide an efficient, practical, and sustainable manufacturing process to synthesize high yields of pure organic carbonates directly from the reactor.

The invention will now be described with respect to particular embodiments which are not intended to limit the invention in any way, but which are simply to further highlight or illustrate the invention. All percentages (%) are weight percentages unless otherwise noted.

Examples 1-4

The results presented in Table I for Examples 1-4 show the use of choline chloride catalyst without co-catalyst resulting in propylene carbonate (PC) at high purity (99.5% PC in Example 1) as contrasted with the use of different co-catalysts which gave products of relatively lower purity.

TABLE I

PC Purity Choline Chloride Catalyst Without and With Co-catalyst at 130° C., 45 psi (0.31 MPa)

| Example | Co-catalyst | Mol Co-catalyst | Mol Catalyst | % PC (by GCMS) |
|---|---|---|---|---|
| 1 | None | 0 | 0.05 | 99.5 |
| 2 | Tartaric acid | 0.05 | 0.05 | 98.1 |
| 3 | Triethanolamine | 0.05 | 0.05 | 98.7 |
| 4 | Glycerol | 0.05 | 0.05 | 98.0 |

GCMS refers to gas chromatography-mass spectrometry.

Examples 5-8

The results presented in Table II for Examples 5-8 show that the use of low concentrations of the choline chloride catalyst are effective in the reaction of propylene oxide with $CO_2$ to give propylene carbonate (PC).

TABLE II

Effect of Choline Chloride Catalyst Concentration at 130° C., 45 psi (0.31 MPa)

| Ex. | Mol Catalyst | % PC (GCMS) |
|---|---|---|
| 5 | 0.01 | 98.9 |
| 6 | 0.05 | 99.5 |
| 7 | 0.09 | 98.2 |
| 8 | 0.12 | 98.0 |

Examples 9-11

The results presented in Table III for Examples 9-11 present the results showing that choline chloride catalyst provides a higher purity PC product and shorter reaction completion times as compared with a choline derivative polymer.

TABLE III

Choline Chloride Catalyst v. Other Catalysts at 130° C., 45 psi (0.31 MPa)

| Ex. | Catalyst | Mol Catalyst | % PC (GCMS) | Completion Time (min.) |
|---|---|---|---|---|
| 9 | Choline chloride | 0.09 | 98.2 | 120 |
| 10 | Cocoalkylmethyl[polyoxyethylene (15)] ammonium chloride | 0.13 | 95.3 | 145 |
| 11 | Tetraethylammonium bromide | 0.09 | 97.4 | 300 |

Examples 12

The FIG. presents a graph of the rate of propylene oxide consumption over time comparing the reaction rate of propylene oxide with $CO_2$ with and without a co-catalyst (glycerol) at 0.01 mol % catalyst, 130 C, and 45 psi (0.31 MPa) showing that there is essentially no significant difference in reaction rates between using choline chloride as the only catalyst and using choline chloride together with glycerol as a co-catalyst.

Examples 13-14

The results presented in Table IV for Examples 13 and 14 show the reaction of PO with $CO_2$ using choline chloride catalyst at different temperatures can result in different reaction rates.

TABLE IV

Reaction Rate Comparison 0.09 Mol % Choline Chloride Catalyst 45 psi (0.31 MPa)

| Ex. | Temperature (° C.) | % PC (GCMS) | Completion Time (min) |
|---|---|---|---|
| 13 | 130 | 98.2 | 120 |
| 14 | 100 | 99.7 | 170 |

Example 15

Table V presents the results of using the synthesis method described herein with ethylene oxide (EO) as the reactant with to give ethylene carbonate (EC) as a different cyclic carbonate product.

TABLE V

| Ethylene Carbonate 0.09 mol % Choline Chloride Catalyst at 45 psi (0.31 MPa) | | | |
|---|---|---|---|
| Ex. | Mol Catalyst | Temperature (° C.) | % EC (GCMS) |
| 15 | 0.09 | 110 | 93.3 |

Examples 16-19

Table VI presents the results for Examples 16-19 showing various carbonates run in the presence of choline chloride catalyst but without a co-catalyst in a PC solvent demonstrating the synthesis of other cyclic carbonates.

TABLE VI

| Various Carbonate Products | | | | | |
|---|---|---|---|---|---|
| Ex. | Epoxide | Mol Catalyst | Temp. (° C.) | % PC (GCMS) | % Other carbonate |
| 16 | Styrene oxide | 0.10 | 100 | 44.8 | 52.2 |
| 17 | Glycidol | 0.05 | 60 | 66.5 | 29.6 |
| 18 | Epichlorohydrin | 0.05 | 100 | 53.2 | 46.0 |
| 19 | 1,2-Epoxydodecane | 0.10 | 120 | 38.4 | 59.0 |

The Examples thus demonstrate how cyclic carbonates may be advantageously directly synthesized by an epoxide with $CO_2$ in the presence of a choline catalyst at mild conditions without the need for a co-catalyst or hydrogen bond donor, in cyclic carbonate solvent.

In the foregoing specification, the invention has been described with reference to specific embodiments thereof, and has been described as effective in providing methods and compositions for directly synthesizing cyclic carbonates. However, it will be evident that various modifications and changes can be made thereto without departing from the broader scope of the invention. Accordingly, the specification is to be regarded in an illustrative rather than a restrictive sense. For example, specific epoxides, choline catalysts, cyclic carbonate products, cyclic carbonate solvents, proportions, reaction conditions, and other components and procedures falling within the claimed parameters, but not specifically identified or tried in a particular method or composition, are expected to be within the scope of this invention.

The present invention may suitably comprise, consist or consist essentially of the elements disclosed and may be practiced in the absence of an element not disclosed. For instance, there may be provided a method for the direct synthesis of cyclic carbonates comprising, consisting essentially of, or consisting of reacting at least one epoxide with carbon dioxide in the presence of a choline catalyst at a temperature between about 25° C. to 150° C. and a pressure of from about atmospheric to 75 psi, in a cyclic carbonate solvent, and then recovering at least one cyclic carbonate product, where the choline catalyst is selected from the group consisting of choline chloride, choline bromide, choline iodide, choline bitartrate, choline citrate, and combinations thereof.

In another non-restrictive version, the only catalyst is the choline catalyst.

The words "comprising" and "comprises" as used throughout, are to be interpreted to mean "including but not limited to" and "includes but not limited to", respectively.

As used herein, the singular forms "a," "an," and "the" are intended to include the plural forms as well, unless the context clearly indicates otherwise.

As used herein, the term "about" in reference to a given parameter is inclusive of the stated value and has the meaning dictated by the context (e.g., it includes the degree of error associated with measurement of the given parameter).

As used herein, the term "and/or" includes any and all combinations of one or more of the associated listed items.

What is claimed is:

1. A method for direct synthesis of cyclic carbonates comprising:

reacting at least one epoxide with carbon dioxide in the presence of a choline catalyst at a temperature between about 25° C. to 150° C. and a pressure of from about atmospheric to 75 psi (0.52 MPa), in a cyclic carbonate solvent; and recovering at least one cyclic carbonate product.

2. The method of claim 1 where the at least one epoxide is selected from the group consisting of ethylene oxide and propylene oxide.

3. The method of claim 1 where the direct synthesis is achieved with the choline catalyst as the only catalyst.

4. The method of claim 1 where the direct synthesis is achieved in the absence of a co-catalyst or a hydrogen bond donor.

5. The method of claim 1 where the reacting is conducted at a temperature in the range of from about 50° C. to about 145° C. and the pressure is from about 30 psi (0.21 MPa) to about 50 psi (0.34 MPa).

6. The method of claim 1 where the concentration of choline catalyst in the solvent ranges from about 0.3 mol % to about 10 mol %, based on the epoxide.

7. The method of claim 1 where the molar ratio of epoxide to carbon dioxide ranges from about 1:1 to about 1:1.2.

8. The method of claim 1 where the choline catalyst is choline chloride.

9. The method of claim 1 where the cyclic carbonate solvent is the same as the cyclic carbonate product.

10. A method for direct synthesis of cyclic carbonates comprising:

reacting at least one epoxide with carbon dioxide in the presence of a choline catalyst at a temperature between about 25° C. to 150° C. and a pressure of from about atmospheric to 75 psi (0.52 MPa), in a cyclic carbonate solvent, where the molar ratio of epoxide to carbon dioxide ranges from about 1:1 to about 1:1.2; and recovering at least one cyclic carbonate product;

where the choline catalyst is choline chloride, and where the at least one epoxide is selected from the group consisting of ethylene oxide and propylene oxide.

11. The method of claim 10 where the direct synthesis is achieved with the choline catalyst as the only catalyst.

12. The method of claim 10 where the concentration of choline catalyst in the solvent ranges from about 0.3 mol % to about 10 mol %, based on the epoxide.

13. The method of claim 10 where the cyclic carbonate solvent is the same as the cyclic carbonate product.

14. A method for direct synthesis of cyclic carbonates comprising:

reacting at least one epoxide with carbon dioxide in the presence of a choline catalyst at a temperature between about 50° C. to about 145° C. and a pressure of from about 30 psi (0.21 MPa) to about 50 psi (0.34 MPa), in a cyclic carbonate solvent; and recovering at least one cyclic carbonate product.

15. The method of claim 14 where the at least one epoxide is selected from the group consisting of ethylene oxide and propylene oxide.

16. The method of claim 14 where the direct synthesis is achieved with the choline catalyst as the only catalyst.

17. The method of claim 14 where the concentration of choline catalyst in the solvent ranges from about 0.5 mol % to about 10 mol %, based on the epoxide.

18. The method of claim 14 where the molar ratio of epoxide to carbon dioxide ranges from about 1:1 to about 1:1.2.

19. The method of claim 14 where the choline catalyst is choline chloride.

* * * * *